United States Patent
Okuyama et al.

(10) Patent No.: US 7,109,020 B2
(45) Date of Patent: Sep. 19, 2006

(54) LEGUMINOUS BACTERIUM HAVING POTENTIATED NITROGEN FIXATION ABILITY

(75) Inventors: Hidetoshi Okuyama, Hokkaido (JP); Takuji Owada, Hokkaido (JP); Nobutoshi Ichinose, Hokkaido (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/483,225

(22) PCT Filed: Jul. 9, 2002

(86) PCT No.: PCT/JP02/06950

§ 371 (c)(1), (2), (4) Date: Feb. 26, 2004

(87) PCT Pub. No.: WO03/006631

PCT Pub. Date: Jan. 23, 2003

(65) Prior Publication Data

US 2004/0241847 A1   Dec. 2, 2004

(30) Foreign Application Priority Data

Jul. 10, 2001  (JP)  ............................ 2001-209214

(51) Int. Cl.
*C12N 1/20* (2006.01)
*C12N 1/21* (2006.01)

(52) U.S. Cl. .................. 435/252.3; 435/410; 435/419; 435/420; 435/243; 435/252.1; 435/252.3

(58) Field of Classification Search ............ 435/320.1, 435/410, 243, 252.2, 252.3
See application file for complete search history.

(56) References Cited

FOREIGN PATENT DOCUMENTS

JP   2000-316584   * 11/2000

OTHER PUBLICATIONS

Yumoto et al. Journal of Fermentation and Bioengineering, vol. 85 No. 1 pp. 113-116, 1998).*
Berendsen (Science. 1998, vol. 282, pp. 642-643).*
Yumoto et al. (Applied and Environmental Microbiology vol. 65 No. 1, 1999, pp. 67-72).*
K. Swaraj et al., "Effect of salt stress on nodulation and nitrogen fixation in legumes", Indian J. Exp. Biol., vol. 37, No. 9, 1999, pp. 843-848.*
N.R. Bishnoi et al., "Influence of sodium chloride on nitrogen fixation and enzymes assocated with scavenging hydrogen peroxide in clusterbean root modules", Indian J. Exp. Biol., vol. 35, No. 2, 1997, pp. 193-196.*
T. Ohwada et al., "Susceptibility to hydrogen peroxide and catalase activity of root nodule bacteria", Biosci. Biotechnol. Biochem., vol. 63, No. 3, 1999.*
T. Owada et al., "Rhizobium fredii USDA191 no Kasanka Suiso Kanjusei to Katalase, Peroxidase Kassei ni tsuite", Taidai Kenpo, vol. 21, No. 1, 1998, pp. 17-25.*
T. Owada et al., "Rhizobium fredii USDA191 no Kasanka Suiso Taisei Hen'ikabu no Konryu Keisei oyobi Chisso Kotei kino ni tsuite", Taidai Kenpo, vol. 21, No. 1, 1998, pp. 27-35.*

* cited by examiner

*Primary Examiner*—Robert A. Zeman
(74) *Attorney, Agent, or Firm*—Wenderoth, Lind & Ponack, L.L.P.

(57) ABSTRACT

The invention of this application provides root nodule bacteria transformed with the DNA fragment of SEQ ID No. 1 consisting a catalase gene and whose nitrogen-fixation ability is enhanced with a catalase produced from the catalase gene, a preparation for leguminous crops containing the root nodule bacteria as an active ingredient, and a method of cultivating leguminous crops which comprises contacting seeds of leguminous crops with these. These inventions enable the acceleration of growth of leguminous crops and multiplication of crop yield of beans. Further, the reduction of agricultural cost and the alleviation of environmental pollution are realized by the reduction of nitrogen fertilizers.

4 Claims, No Drawings

SEQUENCE LISTING

```
<160> NUMBER OF SEQ ID NOS: 1

<210> SEQ ID NO 1
<211> LENGTH: 2354
<212> TYPE: DNA
<213> ORGANISM: Vibrio sp.
<220> FEATURE:
<221> NAME/KEY: gene
<222> LOCATION: (703)..(2232)
<220> FEATURE:
<221> NAME/KEY: CDS
<222> LOCATION: (703)..(2232)
<300> PUBLICATION INFORMATION:
<308> DATABASE ACCESSION NUMBER: GenBank/AB030821
<309> DATABASE ENTRY DATE: 2000-09-02
<300> PUBLICATION INFORMATION:
<310> PATENT DOCUMENT NUMBER: JP2000-316584A
<311> PATENT FILING DATE: 1999-05-14
<312> PUBLICATION DATE: 2000-11-21

<400> SEQUENCE: 1
gtcgacgatg caatgaacgt ccaattcagc cggcacggcc ttgtcgatct cgcgcaggaa      60
cgacaggaat tcctgatggc gatgacgcgg cttgcaagcg gccagcaccg cgccgttgag     120
cacattcagg gccgcgaaca gcgtggttgt gccgtggcgc ttgtaatcgt gagtgacgcc     180
ttcgacgtag cccaggccca tgggcaacat cggctgcgtc cgctccagcg cctggcattg     240
actcttctca tccacgcaca gcaccagtgc gttctcgggc gggctcagat acaggcccac     300
cacgtcgcgc agtttctcca cgaagaacgg gtcgttggac agcttgaagc tctcggtgcg     360
atgcggctga agcccaaaga gctggaagta gcgctgcacg ctgctcttgg agatgccagt     420
ctcagcggcc accgatcgca cgctccagtg cgtcgcgccg tcggccggct tggtgtgcag     480
cgtcgtcttg atcaggctgg ccacgcgctc gtcgtcgatg tgcccggcgg gccgggacgc     540
atgtcgtcgt aaagccccgc aatgcggcgc tcgatgaaac gagcgcgcca cttgcccact     600
gtggccttgg tcagttgcag gcgctcggcg atcgagctgt tggcttcgcc gtcagactag     660
```

-continued

```
tctataattg ttgatggccc cacaaccaat taggagaaat tt atg agc gac gac        714
                                                 Met Ser Asp Asp
                                                  1 acc aaa aag tgc ccc gta acc cac atg act act gac ttc ggc gcc ccc        762
Thr Lys Lys Cys Pro Val Thr His Met Thr Thr Asp Phe Gly Ala Pro
 5              10                  15                  20 gtg gtc act aac cgc gac agc ctc act gca ggt cct cgc ggc ccc tta        810
Val Val Thr Asn Arg Asp Ser Leu Thr Ala Gly Pro Arg Gly Pro Leu
                25                  30                  35 ttg gct cag gat gtc tgg ctg aat gaa aag ctg gcc ggt ttt gtg cgc        858
Leu Ala Gln Asp Val Trp Leu Asn Glu Lys Leu Ala Gly Phe Val Arg
            40                  45                  50 gag gtc atc cca gag cgc cgc atg cac gcc aag gga tcg ggt gcc ttc        906
Glu Val Ile Pro Glu Arg Arg Met His Ala Lys Gly Ser Gly Ala Phe
        55                  60                  65 ggc aca ttc acg gtc acg cac gac atc acc aag tac acc cgc gct aag        954
Gly Thr Phe Thr Val Thr His Asp Ile Thr Lys Tyr Thr Arg Ala Lys
    70                  75                  80 att ttc agc gag gta gga aag aag acg gag atg ttt gcc cgc ttc act       1002
Ile Phe Ser Glu Val Gly Lys Lys Thr Glu Met Phe Ala Arg Phe Thr
85                  90                  95                 100 acg gta gct ggg gag cgc ggt gcg gcc gat gcc gag cgc gat atc cgt       1050
Thr Val Ala Gly Glu Arg Gly Ala Ala Asp Ala Glu Arg Asp Ile Arg
                105                 110                 115 ggt ttt gct ctg aag ttc tat acc gaa gag gga aac tgg gac atg gtg       1098
Gly Phe Ala Leu Lys Phe Tyr Thr Glu Glu Gly Asn Trp Asp Met Val
            120                 125                 130 ggc aat aac act ccg gtg ttc ttc atc cgc gat cct cgc cag ttc cct       1146
Gly Asn Asn Thr Pro Val Phe Phe Ile Arg Asp Pro Arg Gln Phe Pro
        135                 140                 145 gat ctg aat aag gcc gtc aaa cgc gac cct cgc aca aac ttg cgc agc       1194
Asp Leu Asn Lys Ala Val Lys Arg Asp Pro Arg Thr Asn Leu Arg Ser
    150                 155                 160 gcc acc aac aat tgg gat tac tgg acg ctt ctg ccc gaa gct ctg cac       1242
Ala Thr Asn Asn Trp Asp Tyr Trp Thr Leu Leu Pro Glu Ala Leu His
165                 170                 175                 180 caa gtc act gtc gtc atg agc gat cgc ggc atc cct gcc agc tac cgt       1290
Gln Val Thr Val Val Met Ser Asp Arg Gly Ile Pro Ala Ser Tyr Arg
                185                 190                 195 cat atg cac ggt ttc agc tcg cac acc tac agc ctc tgg aac cag gcc       1338
His Met His Gly Phe Ser Ser His Thr Tyr Ser Leu Trp Asn Gln Ala
            200                 205                 210 ggc gag cgt ttc tgg gtc aag atg cat ttc cgg acc cag cag ggc atc       1386
Gly Glu Arg Phe Trp Val Lys Met His Phe Arg Thr Gln Gln Gly Ile
        215                 220                 225 aag aac ctt acc gat gca gag gcc ggc gaa ttg gtc gcc cag gat cgt       1434
Lys Asn Leu Thr Asp Ala Glu Ala Gly Glu Leu Val Ala Gln Asp Arg
    230                 235                 240 gaa agc cat cag cgc gat ctg tat gaa gcc atc gaa cgt ggc gaa tat       1482
Glu Ser His Gln Arg Asp Leu Tyr Glu Ala Ile Glu Arg Gly Glu Tyr
245                 250                 255                 260 ccc aag tgg acg atg ttt att cag gtc atg cca gag gct gat gcg gag       1530
Pro Lys Trp Thr Met Phe Ile Gln Val Met Pro Glu Ala Asp Ala Glu
                265                 270                 275 aag tac gcc ttg cat ccg ttc gat ctg acc aag gtc tgg tac aag ggc       1578
Lys Tyr Ala Leu His Pro Phe Asp Leu Thr Lys Val Trp Tyr Lys Gly
            280                 285                 290 gac tat ccg ctc atc gaa gtt ggt gag ttc gag ctg aac aaa aac tcc       1626
Asp Tyr Pro Leu Ile Glu Val Gly Glu Phe Glu Leu Asn Lys Asn Ser
        295                 300                 305 gag aac ttt ttc gcc gac gtt gaa cag gtg gcc ttt tcc cct agc aat       1674
Glu Asn Phe Phe Ala Asp Val Glu Gln Val Ala Phe Ser Pro Ser Asn
    310                 315                 320 ctg gta cct ggt atc ggt gtc agt ccg gac cgt atg ctg caa gca cgc       1722
Leu Val Pro Gly Ile Gly Val Ser Pro Asp Arg Met Leu Gln Ala Arg
325                 330                 335                 340 ctt ttc aac tac gcc gat gct cag cgc tat cga ctg ggc gta aat tac       1770
```

```
Leu Phe Asn Tyr Ala Asp Ala Gln Arg Tyr Arg Leu Gly Val Asn Tyr
            345                 350                 355
cac cag atc cct gtc aat cag gct cgc tgc cca gtg cac agc aac cac    1818
His Gln Ile Pro Val Asn Gln Ala Arg Cys Pro Val His Ser Asn His
                360                 365                 370 cgc gat ggt cag ggg cgg gtc gat ggc aac tat ggt gct ttg ccg cac    1866
Arg Asp Gly Gln Gly Arg Val Asp Gly Asn Tyr Gly Ala Leu Pro His
                375                 380                 385
tac gaa ccc aac agc ttt ggc caa tgg cag ggc cag ccg cag ttc tcg    1914
Tyr Glu Pro Asn Ser Phe Gly Gln Trp Gln Gly Gln Pro Gln Phe Ser
            390                 395                 400 gag ccg ccg ctc aag ctc acc ggc aat gca gcc cac tgg agc tac gac    1962
Glu Pro Pro Leu Lys Leu Thr Gly Asn Ala Ala His Trp Ser Tyr Asp
405                 410                 415                 420
aaa gat gac cac aac tac ttc gag caa cct ggc aag ttg ttc cgt cta    2010
Lys Asp Asp His Asn Tyr Phe Glu Gln Pro Gly Lys Leu Phe Arg Leu
                425                 430                 435 atg aac gac ggt cag aag gaa gcg ctt ttt ggc aac acc ggc aga gcc    2058
Met Asn Asp Gly Gln Lys Glu Ala Leu Phe Gly Asn Thr Gly Arg Ala
                440                 445                 450
atg ggc gac gct cca gag ttc atc aag ttc cgt cac atc cgc aat tgc    2106
Met Gly Asp Ala Pro Glu Phe Ile Lys Phe Arg His Ile Arg Asn Cys
            455                 460                 465 cac gcc gca gac cct gca tac ggt gca ggc gta gcc aag gcc ctg ggc    2154
His Ala Ala Asp Pro Ala Tyr Gly Ala Gly Val Ala Lys Ala Leu Gly
            470                 475                 480
atc aac ctt gaa aag gca ctg gcc tca aaa aag gat gac cct atg tac    2202
Ile Asn Leu Glu Lys Ala Leu Ala Ser Lys Lys Asp Asp Pro Met Tyr
485                 490                 495                 500 gga aac cca ctg gtc gcc ctg cct gcg tag taaaagcgcc ggaagtatga      2252
Gly Asn Pro Leu Val Ala Leu Pro Ala
                505 aaaagacctt ggtagacgcc aaggctcttt tctcacaccg tcaactaagt caggttcttc  2312 agtcattggc aagcaacctc atctggtcag atcaatgtcg ac                    2354
```

LEGUMINOUS BACTERIUM HAVING POTENTIATED NITROGEN FIXATION ABILITY

This application is a U.S. national stage of International Application No. PCT/JP02/06950 filed Jul. 9, 2002.

TECHNICAL FIELD

The invention of this application relates to root nodule bacteria whose nitrogen-fixation ability is enhanced by expression of a catalase gene introduced, and a preparation for leguminous crops containing the root nodule bacteria as an active ingredient.

BACKGROUND ART

Leguminous crops such as soybeans, adzuki beans and kidney beans can be grown well even in soil with low nitrogen content by atmospheric nitrogen-fixation resulting from bacteroid formed in the root nodules that are symbiotically formed therein according to infection with root nodule bacteria.

Thus, in addition to utilization of ordinary fertilizers, leguminous crops are generally grown from seeds previously coated with root nodule bacteria.

In order to further accelerate growth of various leguminous crops and multiply crop yield thereof, a screening of root nodule bacteria strains appropriate for various leguminous crops has been strenuously conducted so far. Meanwhile, the development of root nodule bacteria transformed by gene introduction has been attempted. For example, JP-T-2000-514663 disclosed the root nodule bacteria that were modified with incorporation of the trifolitoxin gene and efficient in suppression of growth of other competent root nodule bacteria.

Because of their nitrogen-fixation ability, root nodule bacteria play key role in growth and yield of leguminous crops. In leguminous crops, for example, degree of dependence on root nodule bacteria in nitrogen absorption ranges from 30% to 65%, and is extremely high. Accordingly, root nodule bacteria having enhanced nitrogen-fixation ability are expected to greatly enlarge a possibility of cultivating leguminous crops in various soils or increasing yields thereof. In addition, such efficient nitrogen absorption of leguminous crops with root nodule bacteria necessarily decreases dependence on inorganic nitrogen fertilizers such as ammonium sulfate, and therefore contributes greatly toward reduction of agricultural cost and alleviation of environmental pollution.

However, root nodule bacteria whose nitrogen-fixation ability is enhanced to a practical extent have been provided neither by a screening of novel root nodule bacteria from the natural world nor by a production of modified root nodule bacteria through gene manipulation.

In the meantime, a catalase has an activity to catalyze decomposition of hydrogen peroxide acting harmfully on animal and plant individuals into water and oxygen. The inventors of this application previously isolated new *Vibrio rumoiensis* strain S-1 having quite a strong catalase activity (J. Ferment. Bioeng. 85:113–116, 1998), and further specified the catalase gene of this strain (JP-A-2000-316584; Appll. Environ. Microbiol. 65:67–72, 1999; J. Biosci. Bioeng. 90:530–534, 2000). However, it has been so far unknown that a nitrogen-fixation ability of root nodule bacteria is enhanced by a catalase activity. Besides, root nodule bacteria whose nitrogen-fixation ability is enhanced by introduction of a catalase gene have been absolutely unknown.

The invention of this application has been proposed by concerning above-mentioned circumstances, and aims to provide novel root nodule bacteria whose nitrogen-fixation ability is enhanced by gene introduction.

DISCLOSURE OF INVENTION

At the initial stage of infection with root nodule bacteria, leguminous plants generate cytotoxic hydrogen peroxide. On the other hand, they have an enzyme (catalase) that catalyzes decomposition of hydrogen peroxide. Therefore, root nodule bacteria, which acquire high catalase activity, provide such effective suppression of cytotoxicity of hydrogen peroxide that it is expected to promote growth of leguminous crops and to improve yields of leguminous crops. In fact, since the inventors of this application found potent ability of adhesion to root nodules and nitrogen-fixation for transformant root nodule bacteria in which the catalase gene (vktA) derived from *Vibrio rumoiensis* strain S-1 was introduced, this invention have been accomplished herein.

That is, the invention of this application provides root nodule bacteria transformed with a catalase gene, of which nitrogen-fixation ability is enhanced by a catalase produced from the catalase gene.

In the root nodule bacteria of this invention, a preferable embodiment is that the catalase gene is a DNA fragment containing the base sequence of SEQ ID No. 1 that is the catalase gene derived from *Vibrio rumoiensis* S-1 strain.

Further, the invention of this application provides a preparation for leguminous crops containing the root nodule bacteria as an active ingredient.

Still further, the invention of this application provides a method of cultivating leguminous crops, which comprises contacting seeds of leguminous crops with the above-mentioned root nodule bacteria or the preparation.

BEST MODE FOR CARRYING OUT THE INVENTION

The root nodule bacteria of this invention are transformant bacteria having introduced therein a catalase gene. As the catalase gene, a polynucleotide (genomic DNA, mRNA, cDNA or the like) encoding a catalase produced from various organisms can be used. Many types of the catalase gene are known, for example, as follows: *Legionella pneumophilla*-derived catalase gene (J. Bacteriol. 182:6679–6686, 2000; GenBank AF276752, FEMS Microbiol. Lett. 176:339–344, 1999; GenBank AB017595), *Aspergillus nidulans*-derived catalase gene (J. Bacteriol. 183:1434–1440, 2001; GenBank AF316033), *Pseudomonas fluorescence*-derived catalase gene (FEMS Microbiol. Lett. 200:235–240, 2001; GenBank U72068), *Nicotiana tabacum*-derived catalase gene (Plant J. 11:993–1005, 1997; GenBank U93244), *Straphyrococcus aureus*-derived catalase gene (Microbiology 146:465–475, 2000; GenBank AJ000471, AJ000472), *Xanithomonas campestris* pv. *phaseoli*-derived catalase gene (Gene 241:259–265, 2000; GenBank AF170449), *Synechoccus* Sp.-derived catalase gene (Biochimie 82:211–219, 2000; GenBank AF197161) and the like. Accordingly, the root nodule bacteria of this invention entirely include both the catalase genes already known in the literature, the database or the like, and yet unknown catalase genes which might be identified in future.

The catalase gene to be introduced may additionally contain expression control region (promoter/enhancer) inherently concordant therewith or may be a fusion sequence connected therewith an expression control region of a gene which is expressed in root nodule bacteria with high frequency.

Moreover, one embodiment of the transformant root nodule bacteria in this invention is transformant bacteria in which a DNA fragment, containing the vktA gene and having the base sequence of SEQ ID No. 1, is introduced. Specifically, the root nodule bacteria are, as shown in Example, root nodule bacteria having introduced therein a DNA fragment (4.9 kb) containing the sequence of SEQ ID No. 1 that consists of both coding region and promoter sequence of the vktA gene. The vktA gene can be used by being isolated from *Vibrio rumoiensis* strain S-1 by the method described in JP-A-2000-315684. Alternatively, it can be obtained by a PCR method using synthetic oligonucleotides corresponding to partial regions of both ends of the DNA sequence represented by SEQ ID No. 1 as primers and the strain S-1 genome as a template. It can also be obtained by screening a genome library prepared from *Vibrio rumoiensis* strain S-1 using a probe synthesized on the basis of a partial sequence of SEQ ID No. 1. The cloned vktA gene may be ligated into an appropriate vector and subjected to transformation of root nodule bacteria.

The root nodule bacteria are Gram-negative bacteria that form root nodules by infection in roots of leguminous crops. Known root nodule bacteria species that have the growth promoting effect on the leguminous crops may be used. Specifically, they are microorganisms belonging to the Genus *Rhizobium, Bradyrhizobium, Azorhizorium* or the like. More specifically, they are *Rhizobium meliloti, Rhizobium trifolii, Rhizobium lupini, Rhizobium fredii, Rhizobium loti, Rhizobium leguminosarum, Bradyrhizobium japonicum, Azorhizorium caulinodans* and the like. It is possible that an appropriate amount of these root nodule bacteria are inoculated in a medium (TY medium or the like) which is suitable for their growth, and grown by shaking culture at from 25 to 30° C. for from 12 to 36 hours, and cells are harvested by centrifugation and subjected to transformation.

Introduction of vktA gene into the root nodule bacteria can be conducted by introducing a recombinant vector consisting the introduction gene into root nodule bacteria by conventional method such as an electroporation method, a calcium phosphate method, a liposome method or a DEAE dextran method. Alternatively, as shown in Example, transformant root nodule bacteria can be formed by a transfer method through co-culture with root nodule bacteria, a bacterial host (*E. coli* or the like) carrying recombinant vector and a bacterial host containing helper plasmid.

The thus-formed transformant root nodule bacteria have, as shown in Example, a high nitrogen-fixation ability, and can form root nodules satisfactorily by co-existence of seeds of leguminous crops.

The preparations for leguminous crops in this invention contain the transformant root nodule bacteria as an active ingredient. Specifically, the preparations can be prepared as mixture of the root nodule bacteria of this invention at a concentration of from $10^5$ to $10^8$ cells/ml in a liquid medium (for example, TY medium) viable for growing root nodule bacteria. On the other hand, they can be mixed with an organic or inorganic carrier. Specific examples of the inorganic carrier include akadama tsuchi, calcined akadama tsuchi, Kanuma tsuchi, kuroboku soil, vermiculite, pearlite and zeolite, and that of the organic carrier include peat-moss, charcoal, pulp, straw, bagasse, oil meal, fish meal, bone meal, blood meal, shell fossil and crab shell. The way of fixing root nodule bacteria of this invention on the carrier may be conducted by mixing suspension of the root nodule bacteria. At this time, sufficient content of the root nodule bacteria may be at a concentration of from $10^5$ to $10^8$ cells per grain of the carrier. Further, the stability of the root nodule bacteria can be improved by incorporating 40% or more of water in a mixture of the root nodule bacteria and the carrier. Still further, the storage stability of the root nodule bacteria can be more improved by incorporating charcoal ash or the like as a part of a carrier to adjust pH of the preparations ranging from pH 5.5 to pH 8.0.

The thus-formed preparations can be mixed with seeds before sowing or sprayed in sowing in an agricultural land together with fertilizers.

EXAMPLE

The invention of this application is illustrated specifically in more detail below by referring to Example. However, the invention of this application is not limited by the following Example.

1. Construction of a Recombinant Vector

The DNA fragment of SEQ ID No. 1 containing the vktA gene (catalase coding region) and its promoter sequence was introduced into the vector (pBBR1MCS-2: Gene 166:175–176, 1995) that is adaptable to wide host range. Thus the recombinant vector pBBR1MCS-2:vktA carrying the vktA gene was constructed.

2. Construction of Transformant Bacteria 2.1 Microorganism

As root nodule bacteria (recipient) to be transformed, *Rhizobium leguminosarum* bv. *phaseoli* 2676 (kidney bean bacterium) and *Rhizobium fredii* USDA 191 (soybean bacterium) were used. As a donor, *Escherichia coli* JM109 transformed with the recombinant vector pBBR1MCS-2: vktA was used. As helper plasmid-carrying bacteria, *Escherichia coli* MM294 carrying pRK2013 was used.

2.2 Gene Introduction by Conjugal Transfer:

The recipient, the donor and the helper plasmid-carrying bacteria were subjected respectively to shaking culture (100 strokes/min) on 5 ml of TY medium at 30° C., and grown up to logarithmic growth anaphase. Under aseptic manipulation, 40 μl of respective *Escherichia coli* cultures and 100 μl of the root nodule bacteria culture were mixed in a 1.5-ml microtube, and the mixture was centrifuged at 10,000 rpm for 1 minute to collect cells. After the supernatant was removed, the cells were suspended in 100 μl of sterile water, and centrifuged at 10,000 rpm for 1 minute to wash the cells. The cells were suspended in 100 μl of sterile distilled water, and 50 μl of the mixed cell solution was put on a millipore filter placed on TY agar medium, and mated overnight at 30° C. Then, a filter portion to which the cells were adhered was cut out, put in a 1.5-ml microtube, and completely suspended in 1 ml of sterile distilled water. After the filter was removed, the suspension was centrifuged at 10,000 rpm for 1 minute, and the cells were harvested and further suspended in 1 ml of sterile distilled water. Subsequently, diluted cell solution, which was prepared by $10^5$ times-dilution of the suspension with sterile distilled water, was cultured at 30° C. for from 4 to 5 days while being coated in 100-μl portions on a selective agar medium (Sodium succinate 1.35 g, Sodium glutamate 1.1 g, $K_2HPO_4$ 220 mg, $MgSO_4$ 100 mg, $FeCl_2$ 440 mg, $CaCl_2$ 440 mg, Biotin 0.2 mg/L distilled water (pH 7.0)). A transformant strain of the root nodule bacteria transformed with the vktA was screened.

3. Measurement of Catalase Activity 3.1 Culture Conditions:

A cell solution (preculture medium) at logarithmic growth anaphase obtained from reciprocal shaking culture (100 strokes/min) in TY liquid medium (5 ml) at 30° C. was subjected to main culture performed in TY medium (200 ml) from logarithmic growth anaphase to stationary initial phase at 30° C.

3.2 Preparation of a Cell-Free Extract

Cells were collected from the cultured solution by centrifugation at 4° C. and 9,000 rpm for 10 minutes. Subsequently, the cells were washed twice with 50 mM K-phosphate buffer (KPB: 50 mM $KH_2PO_4$ 8.5 ml, 50 mM $K_2HPO_4$ 91.5 ml, pH 7.8). After washing, the resulting cells were suspended in 1 ml of KPB, and then homogenized by sonication (200 W, 2 min.×8 times). The homogenate was centrifuged at 4° C. and 19,000 rpm for 10 minutes. The resulting supernatant was used in the measurement as a cell-free extract.

3.3 Measurement of a Catalase Activity:

$H_2O_2$ was used as a substrate, and 2.645 ml of $H_2O$, 0.3 ml of 0.5 M KPB (pH 6.9) and 5 µl of 30% $H_2O_2$ were mixed in a quartz cell. The mixture was incubated at 25° C. for 3 minutes to make temperature equilibrium. Then, 50 µl of the cell free extract was added, and enzyme activity was measured from the change in absorbance at 240 nm. A molar extinction coefficient, 0.0436 $M^{-1}cm^{-1}$ of $H_2O_2$ was used.

3.4 Measurement of Protein Amount

According to the method of Bradfoard using Coomassie brilliant blue (CBB), 5 ml of CBB solution was mixed with 100 µl of the cell-free extract, and protein amount was measured from absorbance at 595 nm. A bovine serum albumin was used as standard protein.

3.5 Results:

Catalase activities of *Rhizobium leguminosarum* bv. *phaseoli* 2676 and *Rhizobium fredii* USDA 191 transformed with vktA gene were 7,500 U/mg protein and 6,100 U/mg protein respectively, showing significantly high enzyme activities in comparison to catalase activities (3.4 and 2.9 U/mg protein) of their parent strains.

4. Inoculation of Transformant Root Nodule Bacteria in Leguminous Crops 4.1 Host crops:

Soybeans (cultivar Kitamusume) and kidney beans (cultivar Yukitebou) were used. Their seeds were dipped in 70% ethanol for 2 minutes, and then washed three times with sterile distilled water, further surface-sterilized with 10% sodium hypochlorite, and washed six times with sterile distilled water. Further, seed bags (15×16 cm) were used in cultivation of the respective crops. The seed bags, in which 30 ml of nitrogen-free culture solution (Norris-Date solution) was poured, was totally wrapped with an aluminum foil and autoclaved.

4.2 Bacteria for Inoculation:

Both *Rhizobium leguminosarum* bv. *phaseoli* 2676 (kidney bean bacterium) and *Rhizobium fredii* USDA 191 (soybean bacterium) respectively transformed with the vktA gene was used, and also their parent strains were used. Each of the strains was grown on 5 ml of TY medium (bactotripton 5 g, yeast extract 3 g, calcium chloride 6-hydrate 1.3 g/L) under reciprocal shaking-culture (100 strokes/min) conditions up to logarithmic growth anaphase (detected by 1.0 or more of $OD_{660}$, $10^9$ cells/ml). The cells were diluted to 1,000 times with a sterilized phosphate buffered saline (PBS: 0.7 g $KH_2PO_4$, 6.8 g NaCl and 2.4 g $Na_2HPO_4.12H_2O$/L distilled water (pH 7.0))to adjust a cell density to $10^6$ cells/ml. In this manner, inoculation cell solution was prepared.

4.3 Inoculation of Root Nodule Bacteria in a Host Crop

Two seeds were put in one seed bag, and 1 ml of the inoculation cell solution was sprayed on one seed. The whole bag was wrapped with an aluminum foil, and these were allowed to stand still for photophase 14 hours (at 22° C.) and scotophase 10 hours (at 18° C.). After 6 days, the aluminum foil was removed. The cultivation was carried out with watering sterile distilled water until day 20th, and the Norris-Date solution was properly supplemented after clay 20th.

4.4 Measurement of Nitrogen-fixation Activity:

After inoculation of the root nodule bacteria, the measurement was performed after 40 days (kidney beans) or 50 days (soybeans). The plant was put in a 1,000-ml glass pot, and sealed with a rubber stopper. From inside each pot, 100 ml of air (10% of an air amount in the pot) was removed by aspiration with syringe penetrated through the rubber stopper. The same volume of acetylene was then charged therein. After incubation at 30° C. for 1 hour, 1 ml of the gas sealed in the pot was collected, and an amount of ethylene formed was measured by gas chromatography (Hitachi K53, detector: FID, column: PORAPAK N 50 to 80 mesh, column temperature: 50° C., injection temperature: 150° C., flow rate: 30 ml/min).

4.5 Measurement of Weight of Root Nodules:

After the measurement of nitrogen-fixation activity, the plant was withdrawn from the pot. The root nodules were separated, and dried overnight in a desiccator. The weight (dry weight) thereof was measured.

4.6 Results

Table 1 shows comparison of soybeans inoculated with the root nodule bacterium *Rhizobium fredii* USDA 191 (Tf strain: n=6) transformed with the vktA gene and its parent strain (n=6) with respect to the number of root nodules, the weight of root nodules and the nitrogenase activity (ARA) per plant on each cultivation day. Further, Table 2 shows the similar comparison of kidney beans inoculated with the root nodule bacterium *Rhizobium leguminosarum* bv. *phaseoli* 2676 (Tf strain: n=26) transformed with vktA gene and its parent strain (n=29).

As shown in Table 1, in the soybeans inoculated with the transformant strain, the number of root nodules per plant was significantly increased in comparison to the soybeans inoculated with the parent strain, and an increase in nitrogenase activity was also observed. Meanwhile, as shown in Table 2, in the kidney beans inoculated with the transformant strain, the number of the root nodules was not increased, however a significant increase in nitrogenase activity was identified.

TABLE 1

| | Number of root nodules on each cultivation day (number of days) | | | | | | | Weight of root nodule (mg dry wet) | | ARA (μmol/h · mg) | |
|---|---|---|---|---|---|---|---|---|---|---|---|
| Strain | 18 | 21 | 24 | 30 | 36 | 40 | 50 | per nodule | per plant | per nodule | per plant |
| Parent | 5.5 | 8.6 | 11.3 | 13.3 | 15.7 | 17.1 | 18.8 | 0.61 ± 0.11 | 11.46 ± 1.22 | 0.08 ± 0.03 | 0.87 ± 0.19 |
| Tf | 8.6 | 12.0 | 13.8 | 18.0 | 20.7 | 25.1 | 26.4 | 0.53 ± 0.08 | 13.84 ± 1.79 | 0.09 ± 0.02 | 1.23 ± 0.27 |

TABLE 2

| | Number of root nodules on each cultivation day (number of days) | | | | | | | | Weight of root nodule (mg dry wet) | | ARA (μmol/h · mg) | |
|---|---|---|---|---|---|---|---|---|---|---|---|---|
| Strain | 18 | 21 | 24 | 27 | 30 | 33 | 36 | 40 | per nodule | per plant | per nodule | per plant |
| Parent | 71 | 82 | 88 | 101 | 112 | 120 | 127 | 129 | 0.30 ± 0.03 | 36.6 ± 1.6 | 0.7 ± 0.06 | 25.6 ± 2.0 |
| Tf | 57 | 72 | 78 | 84 | 96 | 104 | 110 | 111 | 0.29 ± 0.02 | 31.6 ± 1.8 | 1.2 ± 0.09 | 36.5 ± 2.7 |

INDUSTRIAL APPLICABILITY

As has been thus far described in detail, the invention of this application provides the root nodule bacteria transformed by introduction of a catalase gene and excellent in nitrogen-fixation ability. The acceleration of growth of leguminous crops and the multiplication of crop yield of beans are enabled thereby. Further, reduction of nitrogen fertilizers thereby encourages the reduction of agricultural cost and the alleviation of environmental pollution.

---

The invention claimed is:

1. Root nodule bacteria transformed with a catalase gene other than those obtained from root nodule bacteria, wherein the nitrogen-fixation ability of the root nodule bacteria is enhanced by a catalase produced from the catalase gene, wherein the catalase gene is a DNA fragment comprising the base sequence of SEQ ID No. 1 and is derived from *Vibrio rumoiensis* S-1 strain.

2. A preparation for leguminous crops, which contains the root nodule bacteria of claim 1 as an active ingredient.

3. A method of cultivating leguminous crops, which comprises inoculating seeds of leguminous crops with the preparation of claim 2, and cultivating the seeds.

4. A method of cultivating leguminous crops, which comprises inoculating seeds of leguminous crops with the root nodule bacteria of claim 1, and cultivating the seeds.

* * * * *